US005572880A

United States Patent [19]

Frustaci et al.

[11] Patent Number: 5,572,880

[45] Date of Patent: Nov. 12, 1996

[54] APPARATUS FOR PROVIDING A CONDITIONED AIRFLOW INSIDE A MICROENVIRONMENT AND METHOD

[75] Inventors: Dominick J. Frustaci, Williamsville; James P. Dominiak, Cheektowaga, both of N.Y.

[73] Assignee: Figgie International Inc., Willoughby, Ohio

[21] Appl. No.: 426,022

[22] Filed: Apr. 21, 1995

[51] Int. Cl.$^6$ .............................. F25D 23/12; F17C 9/02; F17C 9/04; A61M 15/06

[52] U.S. Cl. .......................... 62/259.3; 62/50.2; 62/50.4; 128/201.21

[58] Field of Search .............................. 62/259.3, 86, 89, 62/97, 404, 50.2, 50.4; 128/201.21, 200.24, 202.13, 204.17, 204.25, 205.22

[56] References Cited

U.S. PATENT DOCUMENTS

| | | | |
|---|---|---|---|
| 1,459,158 | 6/1923 | Lisse | 128/201.21 |
| 1,464,319 | 8/1923 | Heylandt | 128/201.21 |
| 2,943,459 | 7/1960 | Rind | 62/97 |
| 2,984,994 | 5/1961 | Hankins | 62/259.3 |
| 2,990,695 | 7/1961 | Leffingwell | 62/50.2 |
| 3,000,191 | 8/1961 | Stark | 62/259.3 |
| 3,049,896 | 8/1962 | Webb | 62/384 |
| 3,064,448 | 11/1962 | Whittington | 62/259.3 |
| 3,117,426 | 1/1964 | Fischer et al. | 62/259.3 |
| 3,161,192 | 12/1964 | McCormack | 126/204 |
| 3,227,208 | 1/1966 | Potter, Jr. et al. | 165/96 |
| 3,869,871 | 3/1975 | Rybalko et al. | 62/178 |
| 4,024,730 | 5/1977 | Bell et al. | 62/259.3 |
| 4,172,454 | 10/1979 | Warncke et al. | 128/142.5 |
| 4,586,500 | 5/1986 | Glynn | 128/204.15 |
| 5,115,859 | 5/1992 | Roebelen, Jr. et al. | 165/10 |
| 5,339,806 | 8/1994 | Beaussant et al. | 128/201.21 |
| 5,361,591 | 11/1995 | Caldwell | 62/50.4 |
| 5,365,745 | 11/1995 | Caldwell | 62/50.4 |
| 5,421,326 | 6/1995 | Rankin et al. | 128/201 |

*Primary Examiner*—William Doerrler
*Attorney, Agent, or Firm*—Hodgson, Russ, Andrews, Woods & Goodyear LLP

[57] ABSTRACT

An apparatus for providing a conditioned airflow inside a microenvironment using a portion of the breathing gas supply diverted to an ejector from a breathing respirator gas stream, is described. The respirator, such as a liquified-gas type respirator, includes an endothermic heat exchanger, and the microenvironment air or ambient air or both is flowed over and contacted with the heat exchanger to condition the air by cooling and dehumidifying it. The conditioned airflow is set up by the ejector which expels a portion of the breathing gas stream into a venturi to create a low pressure zone for entraining the microenvironment air or ambient air. The conditioned airflow is then directed to the user's body to reduce user heat stress. Broadly, the air conditioning apparatus is useful with any housing for a controlled physical environment in which a person or group of people can endure surrounding inhospitable conditions.

31 Claims, 7 Drawing Sheets

APPARATUS FOR PROVIDING A CONDITIONED AIRFLOW INSIDE A MICROENVIRONMENT AND METHOD

BACKGROUND OF THE INVENTION

1. Field of the Invention

The present invention generally relates to an apparatus for cooling a person or group of people in a microenvironment. The microenvironment can comprise a housing for a controlled physical environment in which the person or the group of people can survive under surrounding inhospitable conditions.

One embodiment of the present apparatus provides a conditioned airflow inside a protective suit, such as a fireman's turn-out gear or a Hazardous-Materials (Haz-Mat) suit, by diverting a portion of the breathing respirator gas stream to an ejector. The breathing respirator, such as a liquefied-gas type respirator, includes an endothermic heat exchanger for cooling and/or dehumidification of the air in the protective suit microenvironment. The air in the microenvironment is cooled and dehumidified by circulating the air over and contacting it with a heat exchanger. The circulation is set up by the ejector which expands a diverted portion of the breathing gas across a nozzle and into a venturi to create a low pressure zone for entraining the microenvironment air inside the protective suit. The conditioned air is directed to the user's body and particularly the head and upper torso, resulting in reduced user heat stress.

2. Prior Art

Ejector devices including a venturi used to cool a person wearing a protective suit are known in conventional practice. Examples of prior art ejector devices are found in U.S. Pat. Nos. 2,984,994 to Hankins; 3,064,448 to Whittington; 3,117,426 to Fischer et al. and 3,227,208 to Potter, Jr. et al. However, these ejector devices do not segregate the conditioned microenvironment air within the suit, from the breathing gas flowing to the user. Instead, the prior art ejector devices mix these air streams. Mixing the conditioned microenvironment air with the breathing gas supply is unacceptable in those situations when the user is working in a hostile environment where the ambient air outside the microenvironment can adversely influence the air inside. This can occur, for example, when the user is a firefighter working around a burning structure or a pilot flying a high altitude aircraft.

Also, if the breathable gas mixture produced by the respirator device is oxygen rich, the potential for combustion hazards are eliminated for all intents and purposes since the cooling apparatus of the present invention does not employ electrical means which are known ignition sources. In any prior art air conditioning system using an electrical power supply to drive a motor/blower apparatus, sparking is a possibility. Typically, a brushless type motor is needed in these prior art devices to help reduce the possibility for sparking hazard. Electrical shorts, however, are still viable ignition sources and are not mitigated.

SUMMARY OF THE INVENTION

The cooling apparatus of the present invention is useful for cooling a person or a group of people surrounded by an enclosure, thereby creating a conditioned microenvironment atmosphere. One microenvironment enclosure contemplated by the present invention includes a protective suit, such as fireman's turn-out gear or a Hazardous-Materials (Haz-Mat) suit. The cooling apparatus is associated with a breathing apparatus to divert a small motive gas stream from the breathing gas stream to an ejector having an associated venturi to thereby create a low pressure zone at the venturi. This low pressure zone in turn entrains warm, humid microenvironment air or ambient air or both and contacts it over the relatively cold, endothermic heat exchanger. The microenvironment air is warm and humid due to heat and perspiration generated by the person inside the suit, and due to heat conducted and radiated into the suit microenvironment from the ambient environment. The heat exchanger serves to chill and dehumidify the microenvironment air or ambient air, and the low pressure zone set up at the venturi draws this conditioned air into the venturi. The venturi output is then fed to a discharge plenum that through conduits direct the combined conditioned airflow and the motive gas stream to the head, the upper torso and the hips and legs of the user. In the cooling apparatus of the present invention, there is no mixing of the microenvironment air and the actual breathing gas consumed by the user.

The present conditioning apparatus is self-regulatory in the sense that the greater the level of activity experienced by the person wearing the protective suit, the greater that person's respiratory requirements and therefore the quantity of liquid delivered to the heat exchanger and then the flow rate of the breathable gas to the regulator. Therefore, the greater the quantity of liquid delivered to the heat exchanger, the greater its cold sink capacity. This results in increased heat transfer from the microenvironment air or ambient air to the heat exchanger to ultimately cause the conditioned airflow expelled to the user to have a lower temperature and/or relative humidity.

The cooling apparatus of the present invention is also useful with compressed gas type respirators and the relevant microenvironment need not necessarily be limited to a protective suit. Instead, the microenvironment created by the enclosure can include any housing for a controlled physical environment in which a person or group of people can survive under surrounding inhospitable conditions, such as for example, a passenger compartment in a vehicle, a room or any relatively confined enclosure serving as a housing.

These and other aspects of the present invention will become increasingly apparent to those skilled in the art by reference to the following description and to the accompanying drawings.

DETAILED DESCRIPTION OF THE INVENTION

Turning now to the drawings, 1A to 1C show one embodiment of a combination respiratory and cooling apparatus 10 according to the present invention associated with a protective suit 11, such as a fireman's turn-out gear or protective ensemble. The turnout gear is worn by the fireman to preferably cover and protect the chest, legs, feet, arms, hands, head and neck parts of the body. A flip-up face shield 11A associated with a helmet 11B protects a breathing regulator 38 and associated facepiece 40. The combination respiratory and cooling apparatus 10 is strapped on the back with a harness in a known manner and includes a network of conduits for admitting microenvironment air from within the ensemble to the cooling apparatus and then directing the conditioned airflow to various portions of the body, as will be explained in detail hereinafter.

Figure 1A:
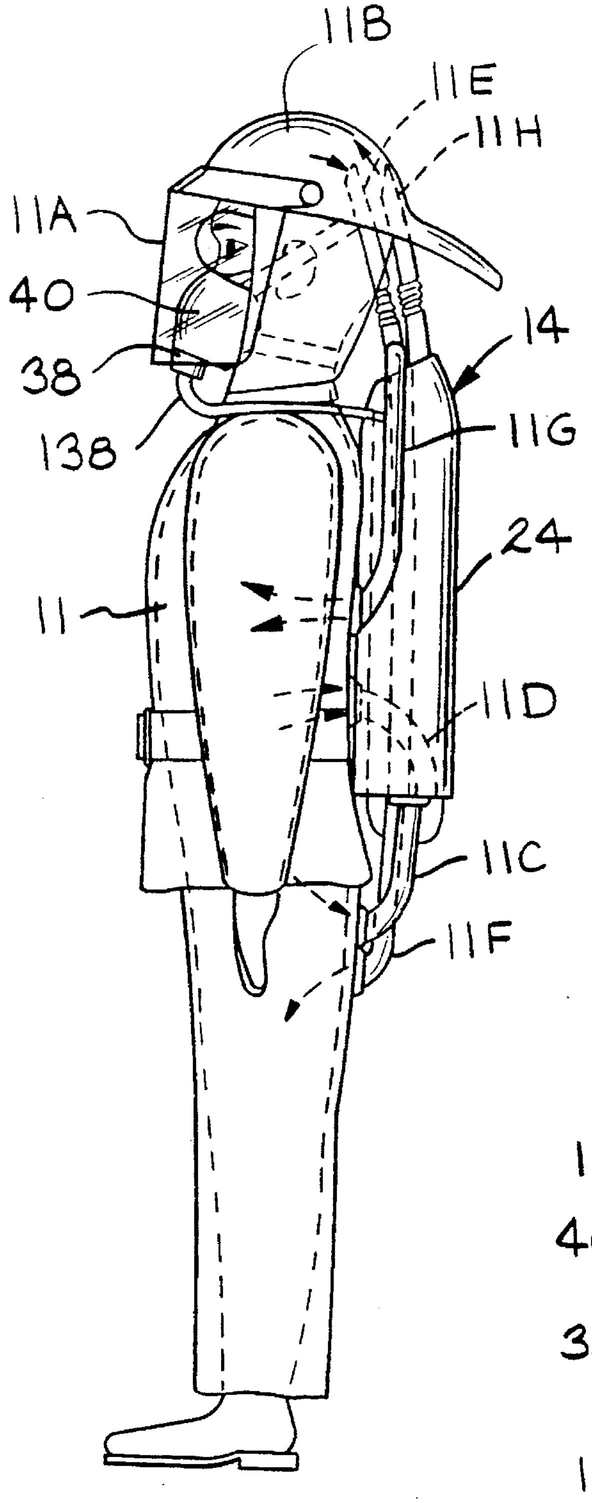
FIG. 1A is a side partial outline view of a user dressed in a fireman's turn-out gear 11 and used in conjunction with a respiratory and cooling apparatus 10 of the present invention.
Figure 1B:
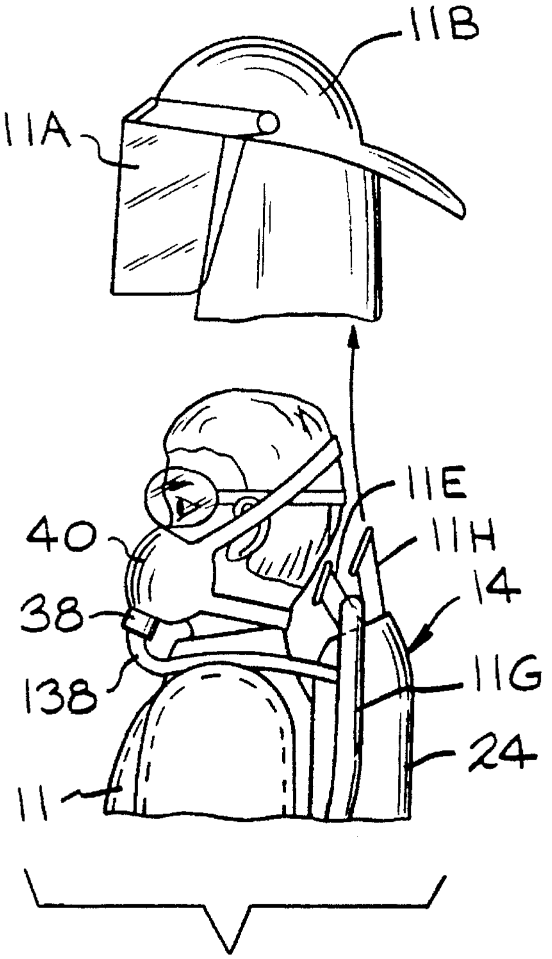
FIG. 1B is a side partial outline and separated view generally similar to FIG. 1A with slightly different head gear removed to indicate the positioning of the airflow conduits.
Figure 1C:
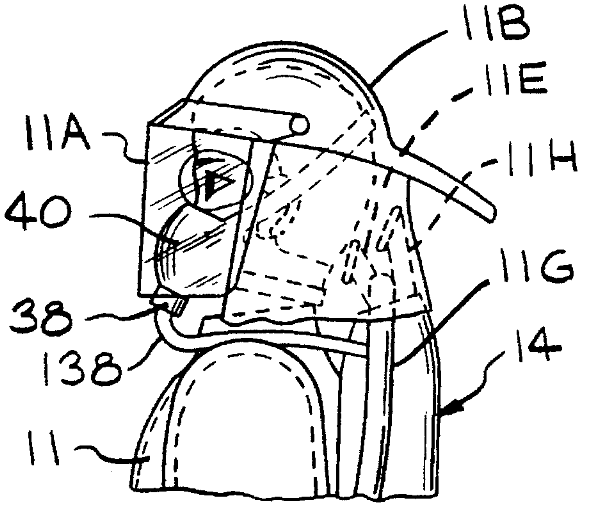
FIG. 1C is a side elevational view of the user shown in FIG. 1B wearing the head gear.
Figure 2A:
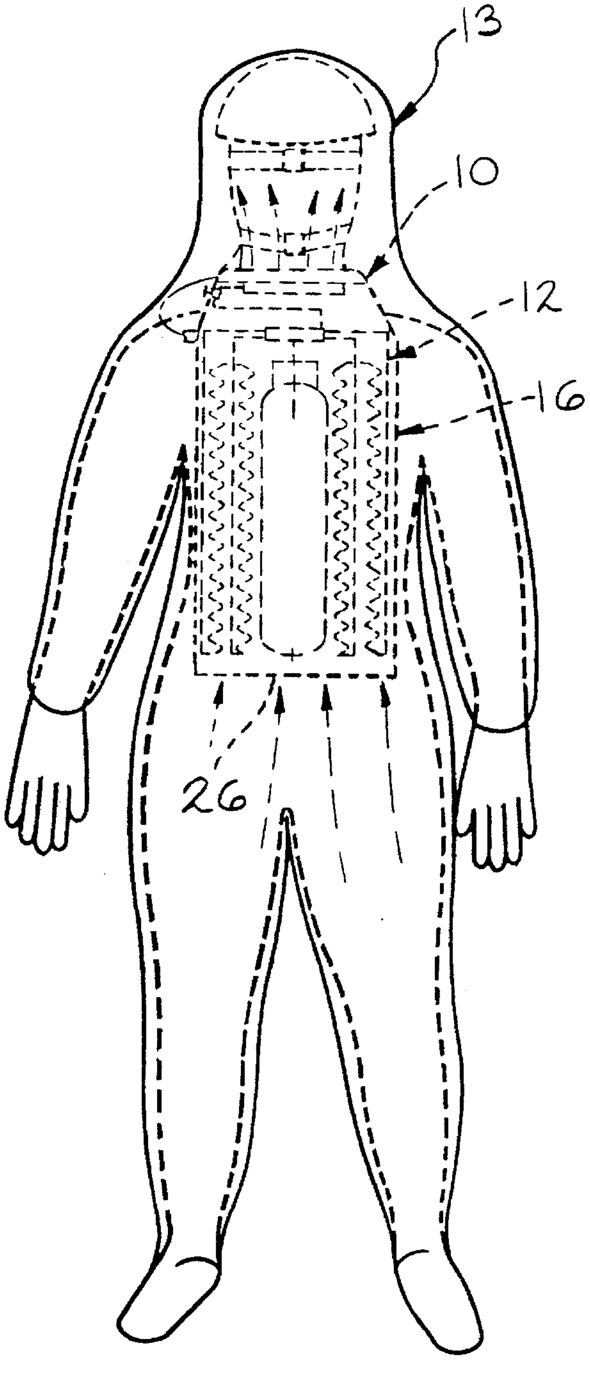
FIG. 2A is a rear outline view of a user dressed in a relatively "loose fitting" full body Haz-Mat suit 13 enclosing the respiratory and cooling apparatus 10 of the present invention.
Figure 2B:
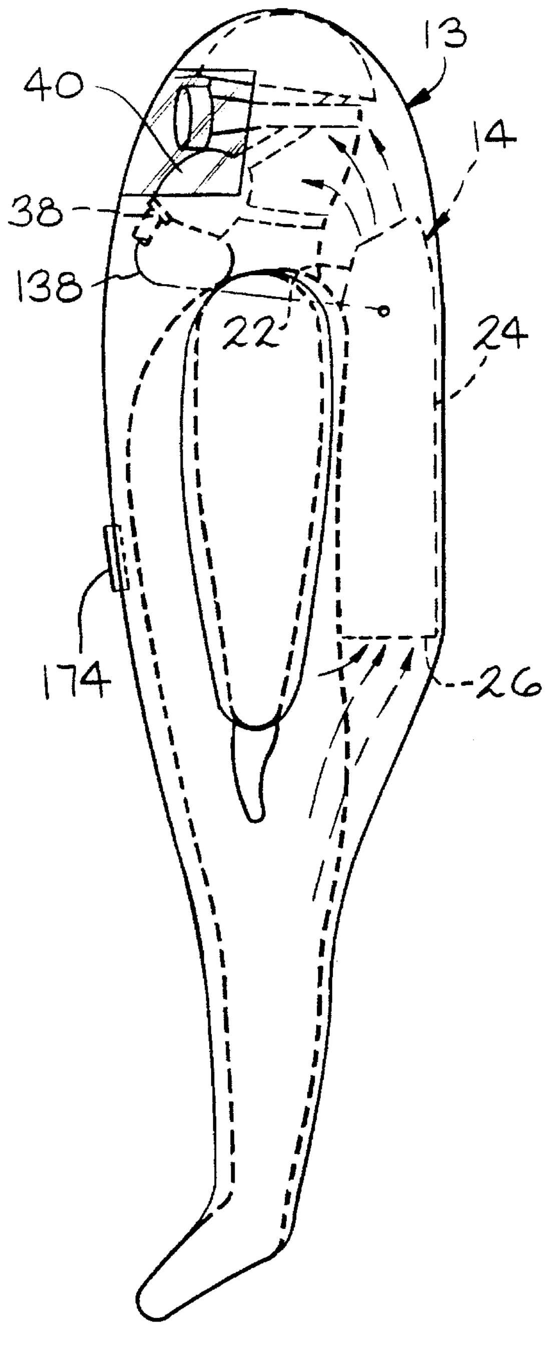
FIG. 2B is a side outline view of the Haz-Mat suit shown in FIG. 2A.

FIGS. 2A and 2B show the combination respiratory and cooling apparatus 10 of the present invention associated with a protective suit 13 such as a relatively "loose fitting", full body Haz-Mat suit. The Haz-Mat suit is worn by the user to preferably cover and protect the entire person including the chest, legs, feet, arms, hands, head and neck parts of the body. The Haz-Mat suit also covers the respiratory and cooling apparatus 10.

While this embodiment of the apparatus 10, shown associated with the fireman's protective ensemble 11 and the Haz-Mat suit 13, is described hereinafter as useful with a Dewar container 12 holding a cryogenic liquid as a breathable gas mixture, it should be understood that the present invention is also useful with any type of cryogenic fluid, supercritical fluid or compressed gas filled in container 12.

Figure 4:
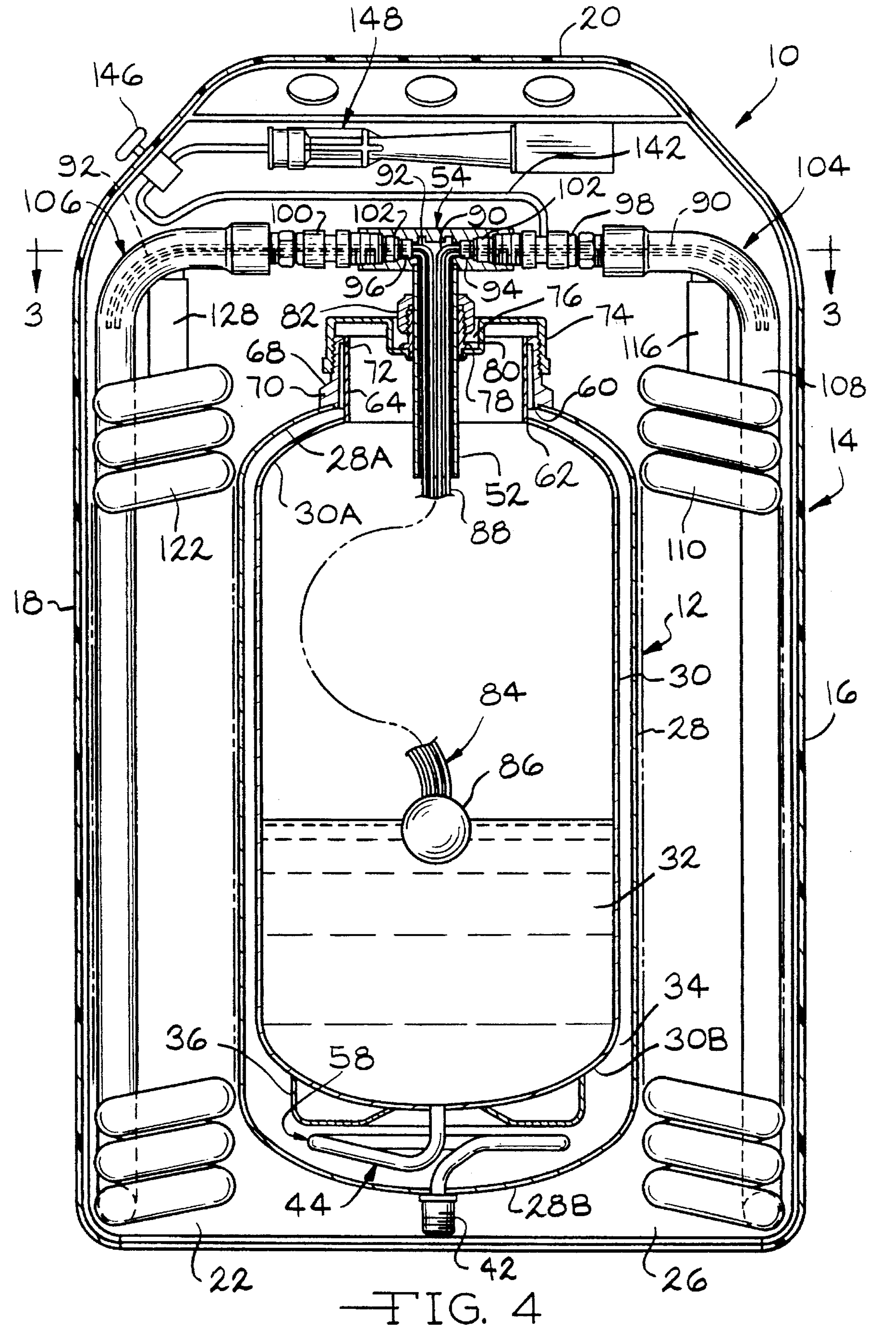
FIG. 4 is a cross-sectional view along line 4—4 of FIG. 3.

As shown in enlarged detail in FIG. 4, the combination respiratory protection and cooling apparatus 10 includes a shroud housing or compartment 14 that encloses the Dewar container 12 and is mounted on the user's back by the harness. The shroud compartment 14 includes spaced apart right and left side walls 16 and 18 extending to and meeting with an upper wall 20 joined to a front wall 22 and a back wall 24 (FIGS. 1A to 1C and 2). The lower portion of shroud 14 is open, as shown at 26, for admitting microenvironment air or ambient atmosphere into the shroud 14. While not shown, it is further contemplated by the scope of the present invention that the back wall of shroud 14 is formed by the back portion of the fireman's turn-out gear 11, or the user's under clothing in the case of the Haz-Mat suit 13, and in that case, the shroud does not necessarily need to be rigid.

FIG. 4 shows the cryogenic liquid Dewar container 12, partly in schematic and partly in cross-section, comprising an outer container means or outer shell 28 mounted around and surrounding an inner container means or inner shell 30 containing the cryogenic liquid 32. The outer shell 28 has a generally cylindrical side wall extending along and around the longitudinal axis of the container 12 with first and second dome portions 28.A and 28B closing the opposed ends thereof. Similarly, the inner shell 30 has a cylindrical side wall extending along and around the longitudinal axis with first and second dome portions 30A and 30B closing the opposed ends thereof. The space 34 formed between the outer and inner shells 28 and 30 is evacuated and provided with an insulation material (not shown) that helps thermally insulate the cryogenic liquid 32. A getter material 36 is mounted on the outside of the second dome 30B of the inner shell 30 to adsorb any residual gases in the evacuated space 34 between the shells 28 and 30. The cryogenic liquid 32 is a liquefied-gas mixture capable of supplying a breathable gas mixture to a breathing regulator 38 and an associated facepiece 40 (FIGS. 1A to 1C and 2).

Figure 3:
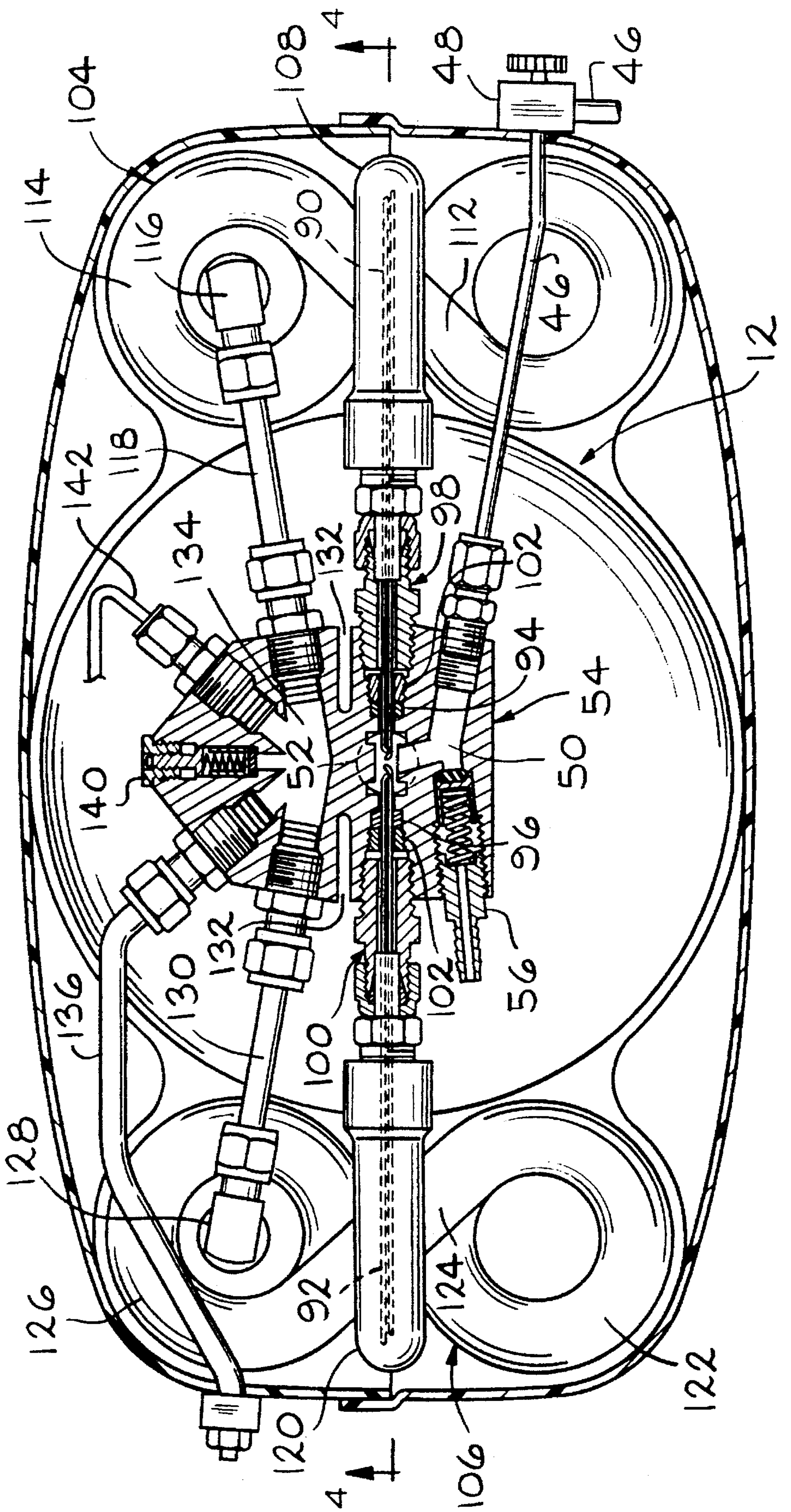
FIG. 3 is a cross-sectional view along line 3—3 of FIG. 4 of a cryogenic liquid Dewar container 12 of the respiratory and cooling apparatus 10 of the present invention.

A liquid fill valve 42 is mounted on the second dome 28B of the outer shell 28. Valve 42 serves as a connection means for connecting the Dewar container 12 to a pressurized liquefied-gas supply (not shown) for filling the cryogenic liquid 32 into the inner shell 30. The valve 42 leads to a gas trap 44 forming a 360 degree loop in the insulating space 34 between the shells 28 and 30. To fill the inner shell with cryogenic liquid 32, the valve 42 is connected to a feed tank (not shown) holding the cryogenic liquid under pressure. Valve 42 is opened and cryogenic liquid 32 is allowed to flow into the inner shell 30 until the liquid is expelled through a vent conduit 46 having an in line valve 48 (FIG. 3). Vent conduit 46 connects to one arm of a branched conduit 50 that in turn connects to a tube 52 supporting a manifold block 54 positioned above the first dome 28A of the inner shell 28, as oriented with respect to FIG. 4. Tube 52 depends into the interior of the inner shell 30, to provide a vent space where a gas pocket forms to prevent the inner shell from being overfilled. Once the cryogenic liquid 32 begins to vent through the tube 52, branched conduit 50, vent conduit 46 and valve 48, the valve 48 is closed. The feed tank remains connected to the inner shell 30 until the pressure inside the inner shell 30 is equalized with that in the feed tank. The pressure of the cryogenic liquid 32 inside the inner shell 30 is preferably at a liquid saturation pressure of about 100 to 130 psig, although the device is capable of functioning with liquid saturated to much lower pressures.

A pressure relief valve 56 connects to the other arm of the branched conduit 50 to communicate with the interior of the inner shell 28. In case of over pressurization of the inner shell, relief valve 56 is set to actuate at about 140 psig.

When valve 42 is closed, the cryogenic liquid 32 fills the trap 44 to about a level marked at 58. The remaining portion of the trap 44 is filled with gas, which is a relatively poor thermal conductor in comparison to the liquid. Independent of the spatial orientation of the container 12, there will always be a high side of the trap 44 that will be filled with gas. The difference between the coefficient of heat transfer of a gas compared to liquid is on the order of magnitude of about ten to as much as a thousand for a boiling liquid. That way, trap 44 helps prevent ambient heat from conducting to the cryogenic liquid 32 in the inner shell 30.

As shown in FIG. 4, a first opening 60 is provided in the upper dome 28A of the outer shell 28 and a second opening 62 is provided in the upper dome 30A of the inner shell 30. The perimeter of opening 60 is spaced from a cylinder 64 having its lower end secured to the perimeter of the second opening 62 aligned along the longitudinal axis of the container 12.

An annular flange 68 has an enlarged base portion 70 secured to the perimeter of opening 60, spaced from the side wall of cylinder 64 with an inwardly extending upper annular rim 72 secured to both the plate 66 and to the cylinder 64 adjacent to their annular connection. A cap 74 is threaded on flange 68. Cap 74 is provided with a central recess 76, a bottom wall 78 of which has an opening. Bottom wall 78 supports a sleeve 80 fitted in a closely spaced relationship around a portion of the tube 52 communicating between the interior of the inner shell 28 and the exterior thereof. A compression nut 82 is threaded on sleeve 80 to secure the tube 52 sealed in place.

Tube 52 partially sheaths a flexible liquid withdrawal conduit means 84 (shown partly in elevation and partly in dashed lines in FIG. 4) having an end disposed inside of a pick-up head means 86 that ensures that the pick-up end of the conduit means 84 is submerged below the surface of the cryogenic liquid 32 during all intended orientations of use of the container 12. The liquid withdrawal conduit means 84 is of a polymeric material that is not adversely affected by contact with the cryogenic liquid 32. Preferably, there are four (or more) withdrawal conduits 84 made of polytetrafluoroethylene having an inside diameter of about 0.020 to 0.040 inches and about a 0.006 to 0.010 inch wall thickness.

As shown in FIGS. 3 and 4, the withdrawal conduits 84 are in fluid flow communication between the pick-up head 86 through tube 52 to an upper end thereof where they separate into two pairs of conduits 90 and 92. Each pair of conduits 90 and 92 pass through a corresponding pressure barrier comprising septum 94 and 96 disposed inside passages in the manifold block 52 and lead into respective heat exchanger conduits 90 and 100. The septa 94, 96 are secured in their passages by nuts 102 threaded into the manifold block 52 with the heat exchanger conduits 98, 100 leading therefrom to respective heat exchangers 104 and 106 mounted adjacent to diametrically opposite portions of the Dewar container 12. The septa 94, 96 insure that there is no fluid communication between the inside of the inner shell 30 and the heat exchanger 104, 106 except that which is transmitted through the liquid conduit pairs 90, 92 themselves. For a more detailed description of the liquid withdrawal conduit means 84 and its associated septum, reference is made to the copending application Ser. No. 08/425,916, filed Apr. 20, 1995 and entitled "Apparatus For Withdrawal Of Liquid From A Container And Method," which is assigned to the assignee of the present invention.

The heat exchangers 104 and 106 each receive about one half of the withdrawn liquid and they serve to transfer heat from the microenvironment atmosphere to the cryogenic liquid, which preferably is a breathable liquefied gas mixture, to vaporize the liquid to a gas and then to warm the gas to a breathable temperature. Heat exchanger 104 is exemplary of the two and it includes an entrance tube portion 108 into which conduit pair 90 empties after passing through septum 94 and heat exchanger conduit 98. Tube 108 flows the cryogenic liquid to a position in the heat exchanger 104 adjacent to opening 26 in shroud 14. The withdrawn liquid flows through a first coiled tube portion 110 to a cross-over tube 112 (FIG. 3), disposed adjacent to entrance tube 108, and to a second coiled tube portion 114. The second coiled portion 114 winds to a position adjacent to the shroud opening 26 to form into an exit tube 116 that passes through the center of the second coiled portion 114 to connect to a warm gas conduit 118 leading to the manifold block 54. The other heat exchanger 106 is similar in construction and, as shown in FIGS. 3 and 4, it includes an entrance tube portion 120, a first coiled portion 122, a cross-over tube 124, a second coiled portion 126 and an exit tube 128 connected to a warm gas conduit 130 leading to the manifold block 54. Preferably, the heat exchanger conduits and the first and second cooled portions of each heat exchanger are fluted to enhance heat transfer while the entrance tube portions and the cross-over tubes are relatively smooth bored.

The manifold block 54 has opposing slits 132 that help reduce conductive heat transfer between the "cold side" supported by tube 52 and a "warm side" supporting a manifold fitting 134 to which the exit tubes 118 and 130 connect. The manifold fitting 134 distributes the warm, breathable gas stream to a discharge conduit 136 leading to a flexible breathing hose 138 that supplies the warmed gas to the breathing regulator 38 and the associated facepiece 40 worn by the user breathing the gas mixture, as indicated in FIGS. 1A to 1C and 2. The warm side of the manifold block 54 also supports a pressure relief valve 140 that is set to actuate at about 110 psig.

Figure 5:
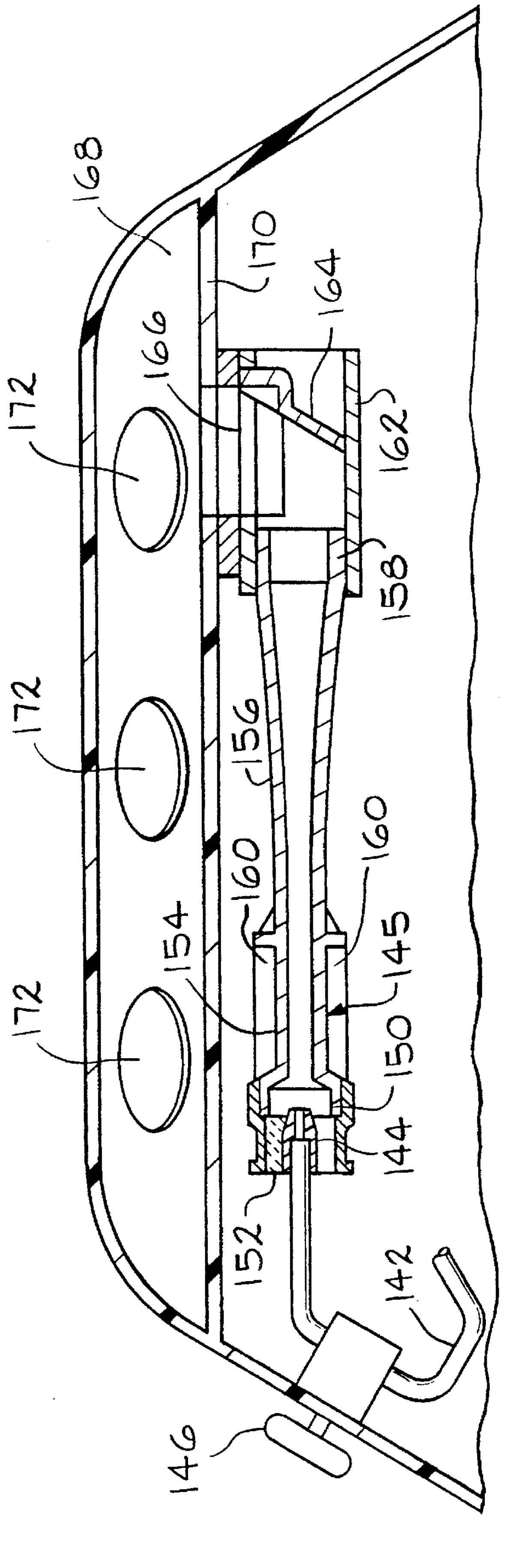
FIG. 5 is partial cross-sectional view of an ejector 144 and venturi 148 of the respiratory and cooling apparatus 10 of the present invention.

As shown in FIGS. 3 to 5, a motive gas conduit 142 branches from the manifold fitting 134 to divert a portion of the breathable gas mixture from the breathing gas stream and provide a motive gas stream directed to an ejector nozzle 144 (FIG. 5). A valve 146 is provided in line between the motive gas conduit 142 and the ejector nozzle 144 to enable the user to regulate the pressure of the motive gas stream delivered to the ejector nozzle 144 and directed to a venturi 148. It should be understood that while valve 146 is shown as a hand operable member, it is contemplated by the scope of the present invention that the valve can be temperature actuated, such as a bimetallic strip, or suitable temperature actuated valve means. Further, valve 146 can be a temperature actuated member with manual override.

The discharge tip of nozzle 144 is supported coaxially inside a bell-shaped housing 150 portion of the venturi 148 by a support 152 mounted therein. Housing 150 joins to a throat or constriction 154 that extends to a frusto-conically outwardly tapered section 156 leading into a ring shaped portion 158 of the venturi 148. Pressure of the gas supplied to the nozzle and the size of the nozzle orifice dictate the flow rate of the motive gas stream.

A plurality of gussets 160 reinforce the housing 150, constriction 154 and part of the tapered section 156. Ring 158 is fitted inside of a cylindrically shaped deflector tube 162 having an internal baffle 164 that deflects the airflow moving through the venturi 148 and into the tube 162 through an outlet opening 166 leading into a plenum chamber 168. The plenum chamber 168 is formed by a horizontally disposed bottom wall 170 which extends between the right and left side walls 16 and 18 and the front wall 22 and back wall 24 of the shroud compartment 14 and spaced below the upper wall 20 thereof. The plenum chamber 168 is completed by the front wall 22 having a plurality of outlet openings 172 that communicate with the interior of the Haz-Mat suit 13 (FIGS. 2A and 2B) to direct the conditioned airflow to the user's body, and particularly the head and upper torso, to thereby provide a cooling airflow to the person wearing the suit. In the case of the fireman's turn-out gear 11 shown in FIGS. 1A to 1C, various conduits 11C, 11D and 11E are provided that draw microenvironment air from proximate the lower body/mid-section of the person, the back and from under the helmet 11B, respectively, to deliver the air to the shroud 14. After the microenvironment air is condition, it is then delivered to the respective body locations conduits 11F, 11G and 11H to cool the body.

It should be understood that the facepiece 40 seals around the perimeter of the user's face in an airtight engagement. That way, the conditioned microenvironment air is prevented from being breathed by the user and is only for the purpose of cooling the user's body to reduce user heat stress. For example, should the user be in a hostile environment where the ambient air may adversely affect the microenvironment air inside the protective suits 11, 13 or where the user's level of work activity adversely affects the microenvironment air, it is imperative that the conditioned airflow remain completely segregated from the breathing gas stream. The Haz-Mat suit 13 is provided with one-way exhalation valves, for example as indicated at 174 in FIG. 2B that expel the conditioned airflow from the suit. In that manner, the protective suit 13 is prevented from becoming over pressurized and the conditioned airflow is maintained.

In use, the protective suits 11, 13 are worn by the user to protect the body from airborne contaminants such as hazardous gases, vapors, liquid contaminants, radiant heat and the like. In that respect, Dewar container 12 is intended for use by a person needing to breath in a hostile environment. The inner shell 30 has previously been charged with a quantity of cryogenic liquid 32, which is a breathable gas mixture. For example, the cryogenic liquid 32 is filled into the inner shell 30 at a liquid saturation pressure of about 100 to 130 psig.

The user first dons the respirator which includes the facepiece 40 while the container 12 and associated heat exchangers 104 and 106 and the shroud compartment 14 is carried on the back by a harness. In the case of the fireman's turn out gear 11, this assembly is carried on the back over the suit by a harness. In the case of the Haz-Mat suit 13, after the container 12 and shroud 14 are harnessed on the user's back, the user dons the protective suit 13 to completely encase his body and the Dewar container 12 and shroud compartment 14. The regulator 38 associated with the facepiece 40 is then actuated, usually by the user inhaling, and breathing begins.

The pick-up head means 86 ensures that the withdrawal conduit means 84 is always in liquid flow communication with the breathable liquefied gas mixture 32 during all intended orientations of use the container 12. The cryogenic liquid 32 is transmitted to the heat exchangers 104 and 106 by the flexible conduit pairs 90 and 92 of the liquid withdrawal conduit means 84. The heat exchangers 104 and 106 vaporize the cryogenic liquid to a gas and then warm the gas to about ambient temperature. The breathable gas mixture flows from the heat exchangers to the manifold fitting 134 and the discharge conduit 136 and onto the flexible breathing hose 138 leading to the regulator 38 on the facepiece 40. In a steady state condition with no withdrawal from the facepiece 40, the entire system including the liquid withdrawal conduit means 84, the heat exchangers 104 and 106 and the discharge conduit 136 and the breathing hose 138 leading to the facepiece regulator 38 are approximately at the pressure of the saturated liquid, i.e. at about 100 to 130 psig, excluding any pressure drop through the length of the system. A pressure drop of between about 1 to 10 psig from inside the inner shell to the regulator is typical. As is well known to those skilled in the art, the regulator provides the breathing gas to the facepiece 40 while maintaining a positive pressure inside the facepiece of about 0 to 2 inches water column above the pressure outside the facepiece.

On demand, for instance, as the result of an inhalation event, a reduced pressure is created through the length of each of the heat exchangers 104 and 106 and to the liquid withdrawal conduit means 74. To replace the gaseous volume consumed during the breathing event and to maintain a uniform system pressure (negating hardware pressure drop considerations), cryogenic liquid 32 is drawn up through the withdrawal conduit means 84 and into the first heat exchangers 104 and 106 to there have heat transferred to it to provide a raised-energy fluid. Liquid flow ceases when the pressure in the heat exchanges equilibrates with the pressure of the Dewar contents, i.e., at about 100 to 130 psig. This continues for as long as there is cryogenic liquid 32 in the inner shell 30 and the user is breathing from the facepiece.

The by-products of respiration include the formation of carbon dioxide and water vapor which helps to create a high relative humidity in the microenvironment inside the protective suits 11,13 that can add considerably to the heat stress experienced by the user. Heat transfer from the ambient surroundings through the protective suits 11, 13 to the microenvironment helps to maintain a high relative humidity microenvironment. This high relative humidity prevents liquid generated through perspiration of the individual from vaporizing and thereby inhibiting cooling of the individual through what is commonly referred to as evaporative cooling heat transfer.

With the heat exchangers 104 and 106 permitting heat to be transferred from the microenvironment to the cryogenic liquid 32 and to the gas moving therethrough, the coils comprising the heat exchangers will be at a relatively lower temperature with respect to the microenvironment. Then, to provide a conditioned airflow, the user opens valve 146 to divert a portion of the breathing gas mixture leaving the manifold fitting 134 and flowing into the discharge conduit 136 leading to the flexible breathing hose 138 to flow through the motive gas conduit 142 and out the ejector nozzle 144. Ejector nozzle 144 expels the motive gas stream which expands into the venturi 148 with a concomitant temperature decrease to establish a low pressure zone at the venturi 148. This low pressure zone serves to set up a microenvironment airflow that enters the shroud 14 through the lower opening 26 to flow over and around the heat exchangers 104 and 106 and into the bell-shaped housing 150 portion of the venturi 148.

The microenvironment airflow entering the shroud 14 is relatively warm and humid, and as it flows over and around the heat exchangers 104 and 106, heat is transferred to the relatively low temperature cryogenic fluid moving through the inside of the heat exchangers 104 and 106. This serves to warm the cryogenic fluid in the heat exchangers while simultaneously lowering both the temperature and humidity of the microenvironment airflow to provide the conditioned airflow. The respective entrance tube portions 108 and 120 of the heat exchangers insure that the coldest cryogenic liquid is proximate the shroud opening 26 to maximize heat exchange of the microenvironment air flowing over the heat exchangers 104, 106 through what is known as a counter flow heat exchanger arrangement. Thus, dehumidification occurs through freezing and/or condensing of water vapor from the relatively high humidity, moisture laden microenvironment airflow drawn into the shroud compartment 14 and passed over and around the relatively cold endothermic heat exchangers 104 and 106.

The conditioned air drawn into the bell-shaped housing 150 of the venturi 148 by the low pressure zone mixes with the motive gas stream expelled into housing 150 from nozzle 144. These combined streams then flow into the deflector tube 162 where they are redirected by baffle 164 through opening 166 and into the plenum chamber 168. From the plenum chamber 168, the conditioned airflow and the motive gas stream passes through the plenum openings 172 and into the protective suit 13 to cool and dehumidify the microenvironment air. Preferably, in the Haz-Mat suite 13 the conditioned airflow is directed to at least the head and upper torso of the user. In the case of the fireman's turn-out gear 11, discharge conduits 11F, 11E and 11H deliver the conditioned air to proximate the crotch, back and the head. In either situation, the reduced water vapor content of the microenvironment air or ambient air enhances evaporative heat transfer of the user. Consequently, user heat stress is significantly reduced. Valve 146 serves as a throttle to regulate the motive gas flow in the venturi which in turn affects the total conditioning airflow delivered to the user. In this manner, evaporative cooling from the user's skin is promoted to thereby reduce the user's heat stress.

The present invention also enables the user to regulate the temperature of the breathable gas i.e., in the range of about 30° F. to 50° F., to further enhance reducing user heat stress. This is done by throttling valve 146 to control the volume of the motive gas stream to nozzle 144 to in turn regulate the flow through the heat exchangers 104,106 and thereby regulate the temperature of the breathable gas delivered to the regulator 38 as a function of the heat transfer to the breathing gas flowing through heat exchangers 104, 106.

Figure 5A:
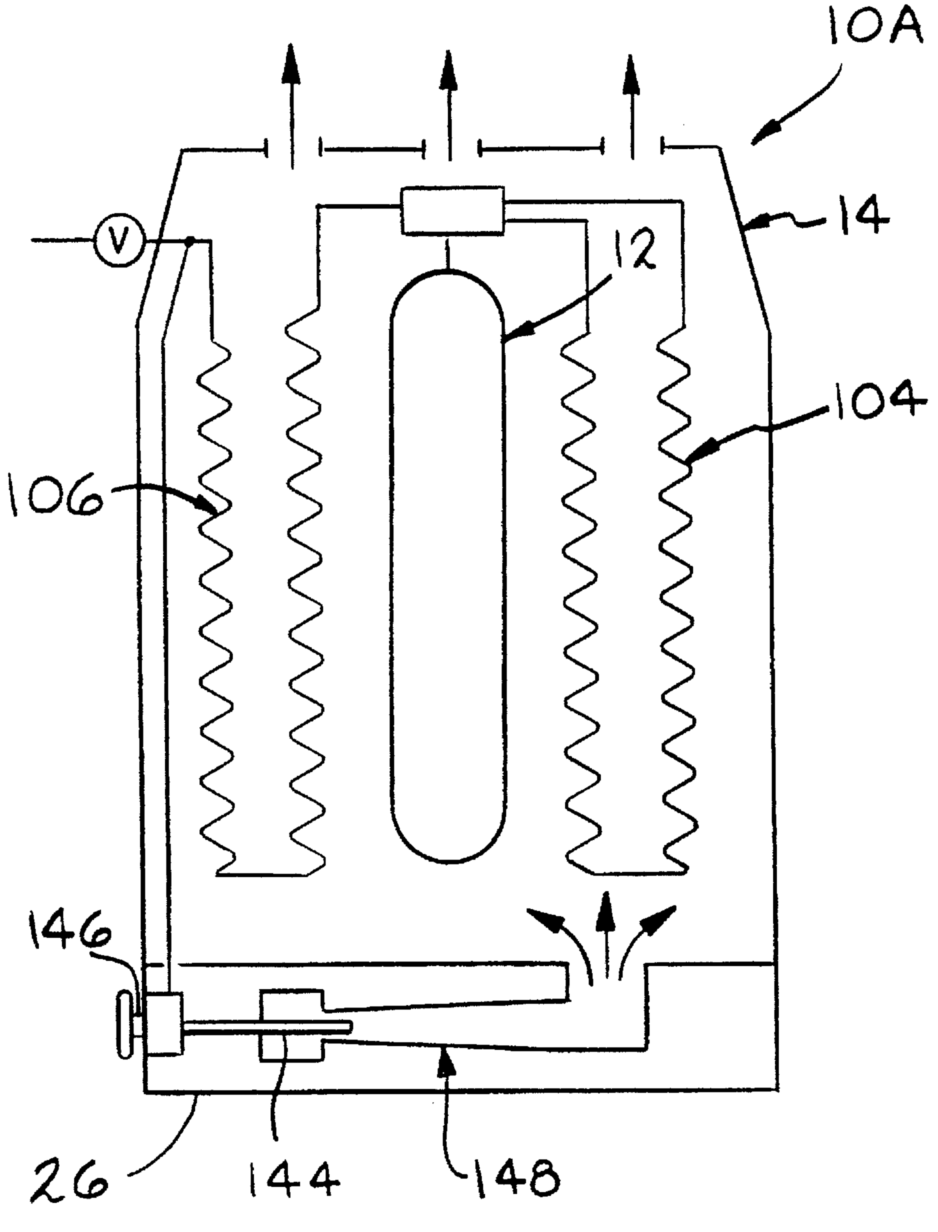
FIG. 5A is a schematic of another embodiment of the respiratory and cooling apparatus 10A of the present invention.

FIG. 5A shows another embodiment of the respiratory and cooling apparatus 10A of the present invention having the ejector nozzle 144 and associated venturi 148 provided adjacent to shroud opening 26 to draw in microenvironment air and/or ambient air before they have been conditioned by contacting the heat exchangers 104,106. The thusly directed combined air flows then pass over the heat exchangers where they are conditioned before flowing out the shroud 14 to cool the user, as previously described.

Thus, the present conditioning apparatus is self-regulatory in the sense that the greater the level of activity experienced by the person wearing the protective suit, the greater that person's respiratory requirements and therefore the quantity of liquid delivered to the heat exchanger and then the flow rate of the breathable gas stream to the regulator. Therefore, the greater the quantity of liquid delivered to the heat exchangers the greater the cold sink attributable to them which results in increased heat transfer from the microenvironment airflow to the heat exchangers. This ultimately cause the conditioned airflow expelled to the user to have a lower temperature and/or relative humidity.

Of course, there may be situations in which the person wearing the suit 11, 13 does not need or desire to use the conditioning apparatus of the present invention. This may occur, for example, when the person's actively level is relatively low and/or the person is working in a relatively cold ambient atmosphere. In that case, the valve 146 remains closed, and respiratory breathing continues from the facepiece 40 supplied with the breathable gas stream transmitted from the heat exchangers and Dewar container.

Figure 6:
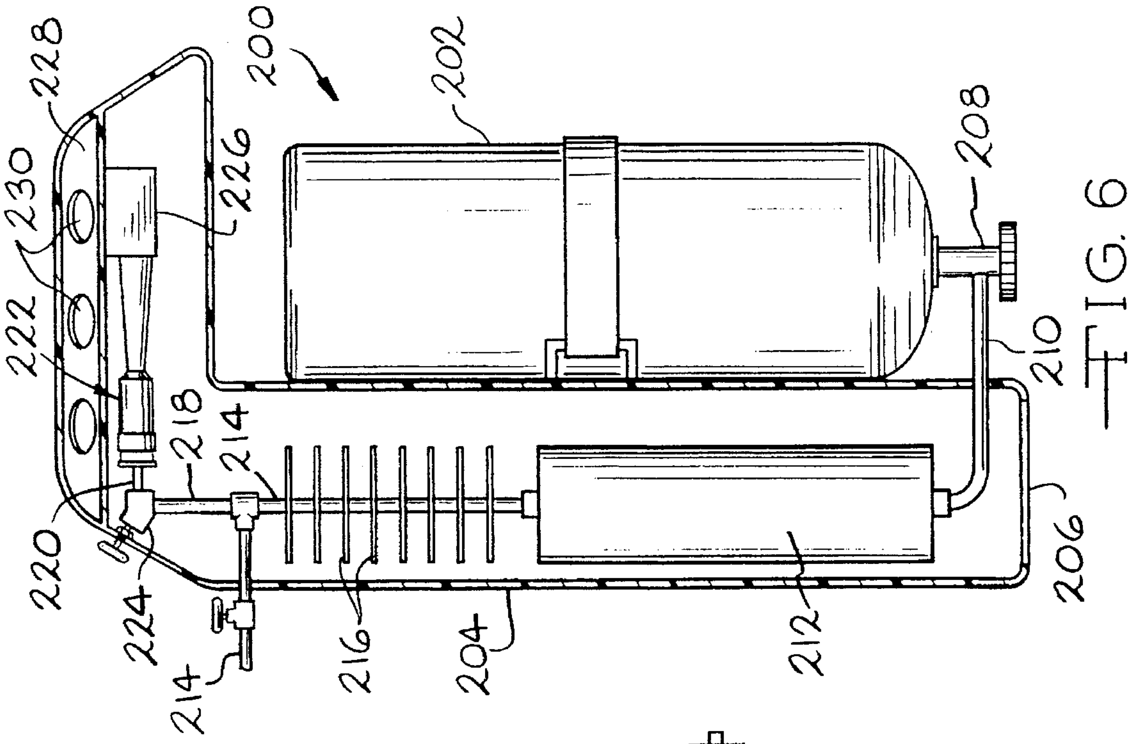
FIG. 6 is a partly schematic and partly cross-sectional view of another embodiment of a respiratory and cooling apparatus 200 of the present invention.

FIG. 6 shows another embodiment of a combination self-contained breathing and air conditioning apparatus 200 according to the present invention comprising a container 202 holding a volume of compressed gas filled therein. The breathing and air conditioning apparatus 200 can be used in conjunction with the protective suits 11, 13, as previously described with respect to the breathing and air conditioning apparatus 10, or with any microenvironment habitat as broadly contemplated by the scope of the present invention.

The breathing and air conditioning apparatus 200 includes the container 202 holding the compressed gas mixture, such as air, to supply a breathable gas mixture to a breathing regulator (not shown) and an associated facepiece (not shown). The container 202 is associated with a shroud housing or compartment 204 having an inverted L-shape with an opening 206 at its lower end thereof.

A valve 208 is provided at one end of container 202 for filling the compressed gas mixture therein and for flowing the compressed gas through a hose 210 leading to a pressure reducer 212. Typically, the compressed gas mixture is at a pressure of about 4,500 psig and the pressure reducer 212 serves to reduce the gas to a pressure of about 110 psig, as is well known to those skilled in the art. As the gas mixture expands, its pressure is reduced and its temperature decreases. This in turn causes the temperature of the pressure reducer 212 itself to decrease. An outboard side of the pressure reducer 212 connects to a discharge conduit 214 provided with a valve 215 and leading to a flexible breathing hose (not shown) that supplies the gas mixture to the breathing regulator and associated facepiece (not shown in FIG. 6) worn by the user breathing the gas mixture. To enhance heat transfer from the microenvironment air to the gas mixture flowing therethrough, conduit 214 has heat exchanger fins 216.

A motive gas conduit 218 branches from the discharge conduit 214 to divert a portion of the breathable gas mixture and provide a motive gas flow directed to an ejector 220 and associated venturi 222. A valve 224 provides for regulating the volume of the motive gas expelled from the ejector 220. Venturi 222 is similar to that shown in FIGS. 4 and 5, and is in fluid flow communication with a deflector tube 226 and a plenum chamber 228 having openings 230 that communicate with the interior of the suits 11, 13. Also, as previously mentioned with respect to valve 146, valve 224 can be a temperature actuated member, such as a bimetallic strip, or a temperature actuated valve with manual override.

In use, the user dons the respirator by donning the facepiece (not shown) while the container 202 and the shroud compartment 204 is carried on the user's back by a harness. In the case of the protective ensemble 11, the assembly is worn outside the turn-out gear and conduits 11C to 11H communicate with the interior thereof, as previously discussed in detail. With the Haz-Mat suite 13, the suit completely encases the body, container 202 and the shroud compartment 204. The regulator (not shown) associated with the facepiece is actuated and breathing across the regulator begins. In that respect, the compressed gas mixture is transmitted through the hose 210 to the pressure reducer 212 where the gas mixture is expanded to decrease its pressure from about 4,500 psig to about 110 psig. This causes the gas temperature to decrease which also reduces the temperature of the pressure reducer 212. With valve 215 in an opened position, the expanded gas mixture flows through the discharge conduit 214 and on to the breathing regulator and facepiece worn by the user breathing the gas mixture.

To provide a conditioning airflow, the user opens valve 224 to divert a portion of the gas mixture to provide a motive gas stream to the ejector 220. Ejector 220 expels the motive gas stream which expands into the venturi 222 with a concomitant decrease in temperature to establish a low pressure zone at the venturi 222. This low pressure zone serves to set up an airflow that draws microenvironment air and/or ambient air into the shroud 204 through the opening 206 to flow over and around the pressure reducer 212 and heat exchanger 216.

The airflow entering the shroud 204 is relatively warm and humid, and as it flows over and around the pressure reducer 212 and heat exchanger 216 heat is transferred from the air to the relatively low temperature gas mixture moving through the pressure reducer 212 and conduit 214. This serves to raise the temperature of the gas mixture flowing therethrough while simultaneously lowering both the thermal energy and humidity of the microenvironment air and/or ambient air to provide the conditioning airflow. Thus, dehumidification occurs through freezing and/or condensing of water vapor from the relatively humid microenvironment air and/or ambient air drawn into the shroud compartment 204 and flowed over and around the relatively cold pressure reducer 212 and heat exchanger 216 to reduce the temperature and humidity of the microenvironment airflow.

The conditioning airflow drawn into the venturi 222 by the low pressure zone mixes with the motive gas stream expelled into the venturi 222 from the ejector nozzle 220. As is the case with the breathing and air conditioning apparatus 10 and the fireman's turn-out gear 11 shown in FIGS. 1A to 1C, these combined air streams then flow into the deflector tube 226 where they are redirected to the plenum chamber 228. From the plenum 228, the combined conditioned airflow and motive gas stream is delivered to selected portions of the body by the conduits 11F to 11H. In the case of the Haz-Mat suit 13 shown in FIGS. 2A and 2B, the combined air streams discharge out the openings 230 into the interior thereof.

To further enhance the conditioning effect of the microenvironment air contacted over the pressure reducer 212 and heat exchanger 216, the compressed gas mixture inside the container 202 may be preconditioned by chilling it to a temperature, for example, of −25° F. prior to delivery to the pressure reducer 212. This increases the heat transfer between the reducer 212 and heat exchanger 216, and the microenvironment air. The pressure reducer 212 can also be provided with fins (not shown) to further enhance this heat transfer.

Figure 7:
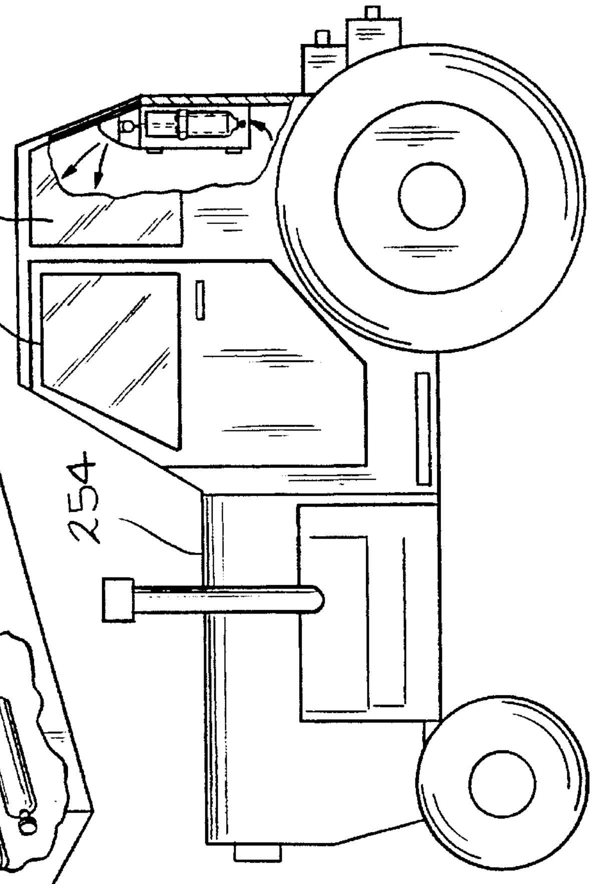
FIG. 7 is a view partly in section and partly in elevation of a cooling apparatus of the present invention provided inside a passenger compartment 250 of a vehicle.

FIG. 7 shows another embodiment of the present invention where the compressed gas container 202 and its associated shroud compartment is used to establish a conditioned airflow in a microenvironment comprising a passenger compartment 250 in a vehicle, such as the cab 252 of a tractor 254. While not shown, the cryogenic fluid container 10 and its associated shroud compartment 14 are similarly useful with the embodiment shown in FIG. 7. However, in this embodiment, there does not necessarily need to be an associated breathing apparatus. Typically, the air inside a compartment such as the tractor cab 252 is not adversely affected to the extent that it is insufficient to support breathing. However, it is often the case that the cab air is warm and humid and this can contribute to the heat stress level of the vehicle operator.

To provide a conditioning airflow for the cab compartment 250, the breathable liquefied gas mixture flows from container 12 through the heat exchangers 104, 106 and into the motive gas conduit 142, or the compressed gas flows through the pressure reducer 212 and heat exchanger 216 to the motive gas conduit 218 and the ejector nozzle 220, as the case may be. Neither the breathable compressed gas nor the breathable cryogenic liquid requires an associated breathing facepiece as long as the air inside the cab 252 is sufficient to support breathing. The ejector 144, 218 expels the gas stream to the venturi 148, 220 such that the expelled gas expands with a concomitant decrease in temperature to establish a low pressure zone inside the venturi 148, 220 and to decrease the temperature of the expelled gas.

As before, this low pressure zone sets up a microenvironment airflow that enters the shroud 14, 204 through its opening 26, 206 and is contacted with around the heat exchangers 104, 106 or over and around the pressure reducer 212 and heat exchanger 216, and then into the respective venturi 148, 220. The heat exchangers 104, 106 and the pressure reducer 212 and heat exchanger 216 are at a relatively low temperature brought about by their respective functions of transferring heat to the cryogenic liquid and expanding the compressed gas with the microenvironment air flowing over and around them to effect heat transfer thereto. The conditioned airflow enters the venturi 148, 222 to mix with the motive gas stream, and both gas streams then flow into the plenum chamber 168, 228 from where they are expelled through openings 172, 230 into the passenger compartment 250 of the cab 252 as the conditioned airflow. If desired, conduits (not shown) are provided for admitting air from various locations in the cab 252 or from the ambient atmosphere, and for delivering the conditioned airflow and motive gas stream back to intended locations in cab 252.

It should be understood that the scope of the present invention need not be limited to use in the cab or passenger compartment of a vehicle or a protective suit, but that the relevant microenvironment is intended to be broadly construed as any housing for a controlled physical environment in which a person or group of people can survive under surrounding inhospitable conditions. Thus, the present invention is intended to be broadly construed as a portable air conditioning apparatus that can be transported with the person and used in a room or other closed compartment in which a conditioned airflow is desired independent of the person's breathing requirements.

With the self-contained breathing and air conditioning apparatus 10,200 of the present invention, very high ambient air entrainment ratios, i.e. ratio of total air conditioning airflow to motive gas flow, on the order of about 12:1 have been achieved. Consequently, only a relatively small amount of the breathing gas mixture is diverted to provide the motive gas flow for the ejector nozzle 144, 220 for driving the air conditioning apparatus 10, 200. This motive gas flow rate can be 10 liters per minute for example while generating a total cooling flow of 120 liters per minute.

It will be apparent to those skilled in the art that as the motive gas is expanded across the ejector nozzle 220, the nozzle 220 will be at a relatively lower temperature with respect to the microenvironment. In the broadest form of the present invention, the microenvironment air is flowed over and around the ejector nozzle 220 to lower both its thermal energy and its humidity to condition the air apart from the conditioning effect of the microenvironment air flowing over the pressure reducer 212 and heat exchanger 216. In that sense, the temperature of the ejector 220 is lowered as the motive gas stream is expelled therefrom and, as the microenvironment airflow circulates over and around the ejector 220, heat is transferred to the ejector 220 to additionally help reduce the temperature of the microenvironment airflow.

The broad concept of flowing microenvironment air over the ejector 220 expelling the motive gas stream to the venturi 222 to condition the microenvironment air can function independent of the user's breathing requirements. In that case, valve 215 regulates the flow through conduit 214 and therefore the flow rate through the pressure reducer 212 to thereby provide a motive gas stream flow through the ejector nozzle 220 at a rate sufficient to set up a conditioning airflow in the protective suit. The gas flow through the reducer 212 must be such that the dependent motive gas flow into the venturi produces a conditioned airflow having a capacity to cool the person to reduce the possibility of heat stroke. Alternatively, the pressure reducer 212 is internally regulated to provide the motive gas flow with a sufficient rate flowing into the venturi 222 to produce a conditioned airflow of a sufficient capacity to cool the person in the protective suit 11,13.

Figure 8:
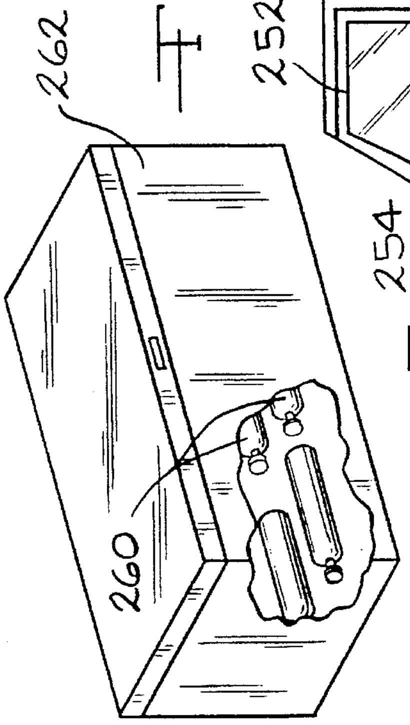
FIG. 8 is a partly broken away perspective view of a freezer unit 262 holding a plurality of compressed gas cylinders 260 useful with the cooling apparatus of the present invention.

FIG. 8 shows another embodiment of the present invention wherein a plurality of compressed gas cylinders 260 containing compressed gas are cooled to a refrigeration temperature in a freezer unit 262. By way of example, the gas pressure can be about 4,500 psig, and the cylinders 260 are refrigerated to a temperature of about −25° F. Then, when the gas is flowed through the pressure reducer 212, expansion further reduces the gas temperature. This "cold" motive gas is then useful with the ejectors 144, 220 and venturis 148, 222, as shown in FIGS. 1 to 6, to set up a conditioning airflow in conjunction with a shroud compartment to cool and dehumidify the air inside a microenvironment.

It is intended that the foregoing description be only illustrative of the present invention and that the present invention be only limited by the hereinafter appended claims.

What is claimed is:

1. An air conditioning apparatus used in conjunction with a breathing apparatus to condition air in a microenvironment, which comprises:

a) supply means for a breathable fluid;

b) heat exchanger means provided outside the supply means and in fluid flow communication with the inside thereof, wherein the breathable fluid is movable from the supply means and through the heat exchanger means to provide a breathable gas stream;

c) respirator means connected to the heat exchanger means to deliver the breathable gas stream to the user to support the user's total respiratory requirements;

d) conduit means connected to the breathable gas stream downstream of the heat exchanger means, the conduit means including a diverter means intermediate the heat exchanger means and the respirator means to divert a portion of the breathable gas stream to an ejector means for expanding the diverted portion of the breathable gas stream to create a motive gas stream;

e) venturi means for receiving the motive gas stream to in turn create a reduced pressure zone at the venturi means; and f) housing means for admitting microenvironment air or ambient air or both therein wherein the reduced pressure zone draws the microenvironment air or the ambient air into the housing means to flow across and contact the heat exchanger means to cool and dehumidify the microenvironment air or the ambient air or both and thereby create a conditioned airflow, and wherein the combined conditioned airflow and the motive gas stream are expelled into the microenvironment to cool the user.

2. The air conditioning apparatus of claim 1 wherein the venturi means is positioned such that the reduced pressure zone provides for the microenvironment air or ambient air or both to contact the heat exchanger means to provide the conditioned airflow and wherein the venturi means serves to expel the conditioned airflow and the motive gas stream into the microenvironment to cool the user.

3. The air conditioning apparatus of claim 1 wherein the venturi means is positioned such that the reduced pressure zone provides for the microenvironment air or ambient air or both to expel from the venturi means before contacting the heat exchanger means to provide the conditioned airflow and wherein the combined conditioned airflow and motive gas stream are movable into the microenvironment to cool the user.

4. The air conditioning apparatus of claim 1 wherein the ejector means is a nozzle means.

5. The air conditioning apparatus of claim 1 wherein the microenvironment is closed.

6. The air conditioning apparatus of claim 5 including at least one inlet conduit means for admitting microenvironment air into the housing means from a first desired location in the microenvironment and further including at least one discharge conduit means for expelling the combined conditioned airflow and the motive gas stream to a second desired location in the microenvironment.

7. The air conditioning apparatus of claim 1 wherein the microenvironment is a partially open system.

8. The air conditioning apparatus of claim 7 including at least one inlet conduit means for admitting either microenvironment air or ambient air or both into the housing from a first desired location and further including at least one discharge conduit means for expelling the combined conditioned airflow and the motive gas stream to a second desired location in the microenvironment.

9. The air conditioning apparatus of claim 1 wherein the diverter means is a valve means.

10. The air conditioning apparatus of claim 9 wherein the valve means is either temperature actuated, manually actuated, or combination thereof.

11. The air conditioning apparatus of claim 1 wherein the breathable fluid in the container means is a cryogenic fluid.

12. The air conditioning apparatus of claim 1 wherein the breathable fluid in the container means is a compressed gas mixture of oxygen and nitrogen.

13. The air conditioning apparatus 1 wherein the venturi means is to fluid flow communication with a plenum means that in turn discharges the conditioned airflow to the microenvironment.

14. The air conditioning apparatus of claim 1 wherein the microenvironment comprises a protective suit worn by the user.

15. The air conditioning apparatus of claim 1 wherein the microenvironment comprises a passenger compartment.

16. The air conditioning apparatus of claim 1 wherein the breathable fluid is refrigerated prior to being moved to the heat exchanger means.

17. A method for conditioning air in a microenvironment in conjunction with a breathing apparatus, comprising:

a) providing an air conditioning apparatus including: a supply for a breathable fluid; and a heat exchanger means provided outside the supply means and in fluid flow communication with the inside thereof;

b) moving the breathable fluid from the supply means and through the heat exchanger means to provide a breathable gas stream;

c) supplying the breathable gas stream to a respirator means worn by the user thereby supplying the user's total respiratory requirements;

d) diverting a portion of the breathable gas stream to an ejector means by actuating a diverter means disposed intermediate the heat exchanger means and the respirator means thereby expanding the diverted portion of the breathable gas stream and creating a motive gas stream delivered to a venturi means which in turn creates a reduced pressure zone at the venturi means, the reduced pressure zone inducing air from the microenvironment or an ambient atmosphere or both to flow across and contact the heat exchanger means to condition the microenvironment air or the ambient air; and e) directing the combined conditioned airflow and the motive gas stream into the microenvironment to cool and dehumidify the user.

18. The method of claim 17 including a housing means having an opening and admitting the microenvironment air or ambient air or both into the housing means through the opening to pass over the heat exchanger means providing the conditioned airflow and flowing the conditioned airflow and motive gas stream to the reduced pressure zone at the venturi means.

19. The method of claim 17 including a housing means having an opening and admitting the microenvironment air or ambient air or both into the housing means through the opening flowing to the reduced pressure zone to expel from the venturi means before contacting the heat exchanger means to provide the conditioned airflow combined with the motive gas stream flowing into the microenvironment to cool the user.

20. The method of claim 17 including directing the combined conditioned airflow and the motive gas stream to a plenum means and then discharging them into the microenvironment from the plenum means to cool and dehumidify the user.

21. The method of claim 17 wherein the microenvironment is closed and including providing at least one inlet conduit means admitting microenvironment air from a first desired location to flow across the heat exchanger means and discharging the combined conditioned airflow and the motive gas stream to expel through at least one discharge conduit means to a second desired location in the microenvironment.

22. The method of claim 17 wherein the microenvironment is a partially open system and including providing at least one inlet conduit means admitting either microenvironment air or ambient air or both from a first desired location to flow across the heat exchanger means and discharging the combined conditioned airflow and the motive gas stream to expel through at least one discharge conduit means to a second desired location in the microenvironment.

23. The method of claim 17 including refrigerating the breathable fluid prior to use.

24. A breathing apparatus, which comprises:

a) supply means for a breathable fluid;

b) heat exchanger means provided outside the supply means and in fluid flow communication with the inside thereof, wherein the breathable fluid is movable from the supply means and through the heat exchanger means to provide a breathable gas stream;

c) housing means provided to contain the heat exchanger means;

d) respirator means connected to the heat exchanger means to deliver the breathable gas stream to the user to support the user's total respiratory requirements;

e) ejector means disposed inside the housing means and fed by a conduit means connected to the breathable gas stream downstream of the heat exchanger means, the conduit means including a diverter means disposed intermediate the heat exchanger means and the respirator means to divert a portion of the breathable gas stream to the ejector means for expanding the diverted portion of the breathable gas stream to create a motive gas stream;

f) venturi means associated with the ejector means for receiving the motive gas stream to in turn create a reduced pressure zone inside the housing means at the venturi means; and g) an opening into the housing means for admitting air outside of the housing means therein, wherein the reduced pressure zone draws the outside air into the housing means through the opening to flow over and contact the heat exchanger means to transfer heat energy to the breathable fluid and provide the breathable gas stream delivered to the user, and wherein after the outside air has contacted the heat exchanger means, the combined outside airflow and the motive gas stream are expelled from the housing means with the reduced pressure zone at the venturi means serving to continuously draw outside air through the opening into the housing means to continuously contact the heat exchanger means to thereby transfer heat energy to the breathable fluid and provide the breathable gas stream.

25. The breathing apparatus of claim 24 with the user breathing inside of a microenvironment and wherein the outside air consists of a microenvironment air or ambient air outside the microenvironment, or both.

26. The breathing apparatus of claim 24 wherein the diverter means is a valve means.

27. The breathing apparatus of claim 24 wherein the valve means is either temperature actuated, manually actuated, or a combination thereof.

28. The breathing apparatus of claim 24 wherein the breathable fluid in the container means is a cryogenic fluid.

29. The breathing apparatus of claim 24 wherein the breathable fluid in the container means is a compressed gas mixture of oxygen and nitrogen.

30. A method for providing a breathable gas stream to a user to support the user's total respiratory requirements, comprising:

a) providing a breathing apparatus including: supply means for a breathable fluid; heat exchanger means provided outside the supply means and in fluid flow communication with the inside thereof; housing means provided to contain the heat exchanger means; and an opening into the housing means for admitting air outside of the housing means therein;

b) moving the breathable fluid from the supply means and through the heat exchanger means to provide the breathable gas stream;

c) supplying the breathable gas stream to a respirator means worn by the user thereby supplying the user's total respiratory requirements;

d) diverting a portion of the breathable gas stream to an ejector means positioned inside the housing means by actuating a diverter means disposed intermediate the heat exchanger means and the respirator means thereby expanding the diverted portion of the breathable gas stream at the ejector means and creating a motive gas stream delivered to a venturi means associated with the ejector means which in turn creates a reduced pressure zone inside the housing means at the venturi means, the reduced pressure zone inducing outside air to flow through the opening into the housing means flowing over and contacting the heat exchanger means to transfer heat energy to the breathable fluid and providing the breathable gas stream delivered to the user; and e) expelling the combined outside airflow and the motive gas stream from the housing means with the reduced pressure zone at the venturi means continuously drawing outside air through the opening into the housing means to continuously contact the heat exchanger means thereby transferring heat energy to the breathable fluid and providing the breathable gas stream.

31. The method of claim 30 with the user breathing inside of a microenvironment and wherein the outside air consists of a microenvironment air or ambient air outside the microenvironment, or both.

* * * * *